United States Patent [19]

Vassiliadis

[11] Patent Number: 4,473,074
[45] Date of Patent: Sep. 25, 1984

[54] MICROSURGICAL LASER DEVICE
[75] Inventor: Arthur Vassiliadis, Palo Alto, Calif.
[73] Assignee: Xanar, Inc., Colorado Springs, Colo.
[21] Appl. No.: 306,268
[22] Filed: Sep. 28, 1981
[51] Int. Cl.³ .............................................. A61B 17/36
[52] U.S. Cl. ................................. 128/303.1; 128/395; 219/121 LQ
[58] Field of Search ...................... 128/303.1, 395–398; 219/121 L, 121 LR, 121 LQ, 121 LP

[56] References Cited

U.S. PATENT DOCUMENTS

| | | | |
|---|---|---|---|
| 3,296,795 | 1/1967 | Nielsen | 219/121 LR |
| 3,348,547 | 10/1967 | Kavanagh | 128/395 |
| 3,528,424 | 9/1970 | Ayres | 128/303.1 |
| 3,642,352 | 2/1972 | Beach | 128/303.1 X |
| 3,703,176 | 11/1972 | Vassiliadis et al. | 128/395 |
| 3,720,213 | 3/1973 | Hobart et al. | 128/395 |
| 3,828,788 | 8/1974 | Krasnov et al. | 128/303.1 |
| 3,910,276 | 10/1975 | Polanyi et al. | 128/303.1 |
| 3,913,582 | 10/1975 | Sharon | 128/303.1 |
| 4,057,332 | 11/1977 | Brubaker et al. | 219/121 LR |
| 4,069,823 | 1/1978 | Isakov et al. | 128/303.1 |
| 4,122,853 | 10/1978 | Smith | 128/303.1 |
| 4,123,143 | 10/1978 | Yachin et al. | 128/303.1 X |
| 4,144,888 | 3/1979 | Malyshev et al. | 128/303.1 |
| 4,174,154 | 11/1979 | Kawasaki | 128/303.1 X |
| 4,270,845 | 6/1981 | Takizawa et al. | 128/303.1 X |

FOREIGN PATENT DOCUMENTS 2827639  1/1979  Fed. Rep. of Germany ... 128/303.1

Primary Examiner—Lee S. Cohen
Attorney, Agent, or Firm—Michael A. Kaufman

[57] ABSTRACT

Microsurgical laser device for guiding a laser beam to a desired target. The device includes a laser head supported in a relatively horizontal orientation by a counterbalanced articulated support arm which provides for elevational positioning of the laser head as well as rotation of the laser head about two parallel spaced apart vertical axes. The support arm, in turn, is rotatably supported by a vertical post defining a third vertical axis.

Threadably connected to one end of the laser head is an articulated laser guide arm having a precision telescopic first section followed by four rotatable mirror sections each of which is adapted to redirect a beam 90° along a plane perpendicular to the axis of the incident path. Each section is precision made to obviate the need to adjust the mirror or align the arm.

The support arm permits easy approximate positioning of the laser head in the vicinity of the laser beam target while the relatively short pre-aligned articulated laser beam guide provides for quick precise aiming of the laser beam.

The vertical post is supported by a base cabinet that contains the power supplies. The controls of the laser beam characteristics such a power level and time of exposure are contained on a moveable control console that is separate from the base cabinet.

7 Claims, 7 Drawing Figures

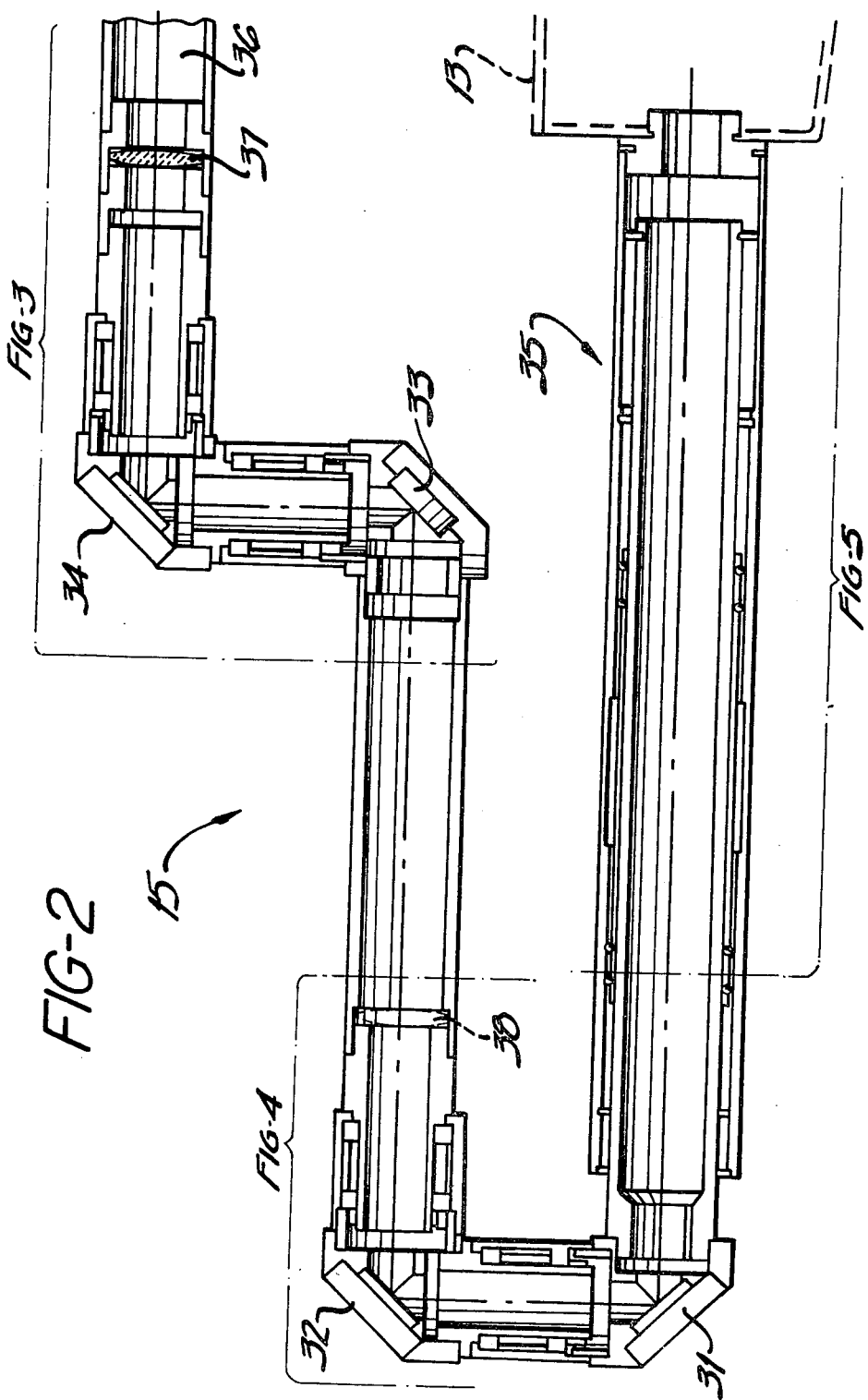

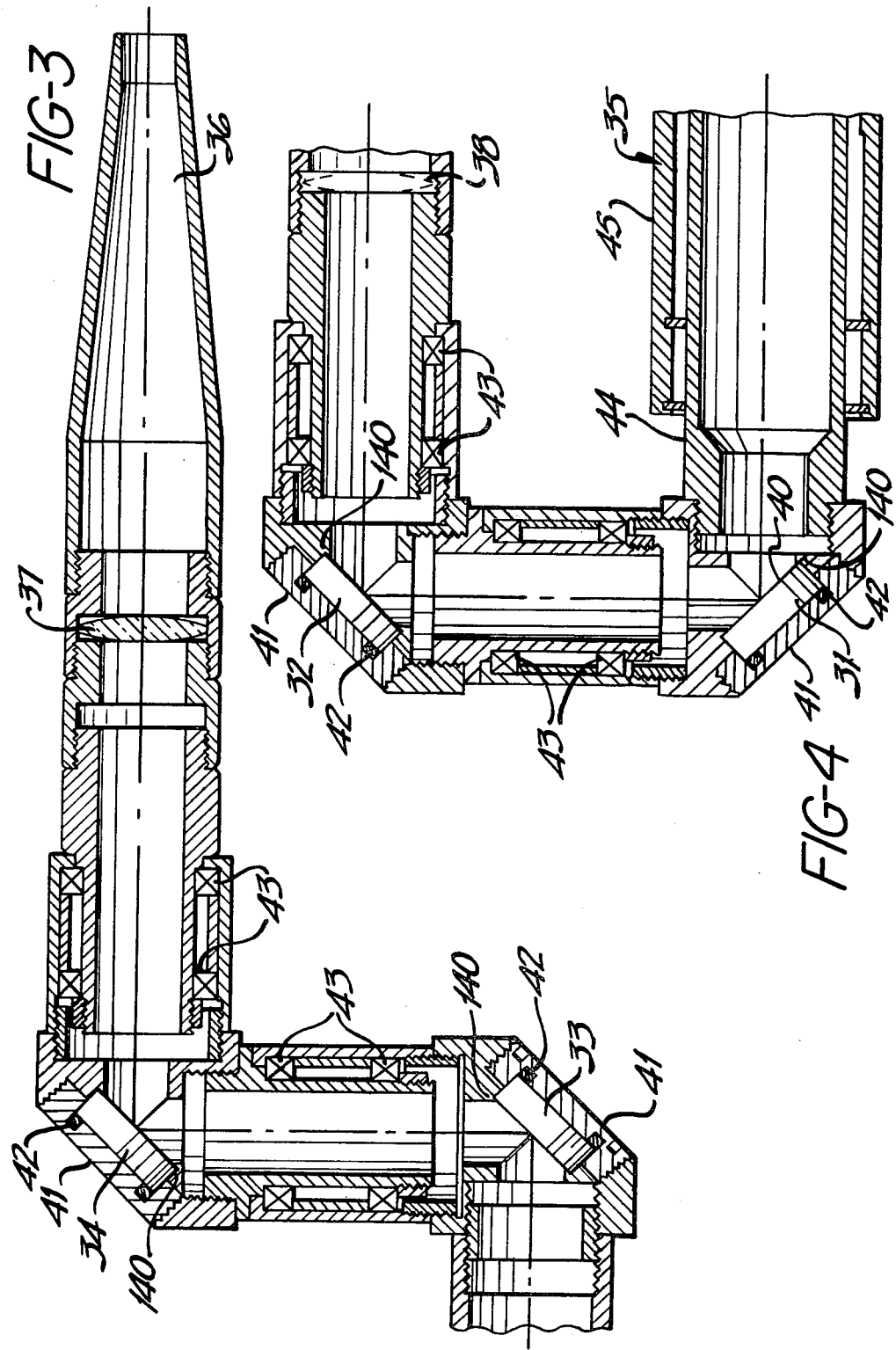

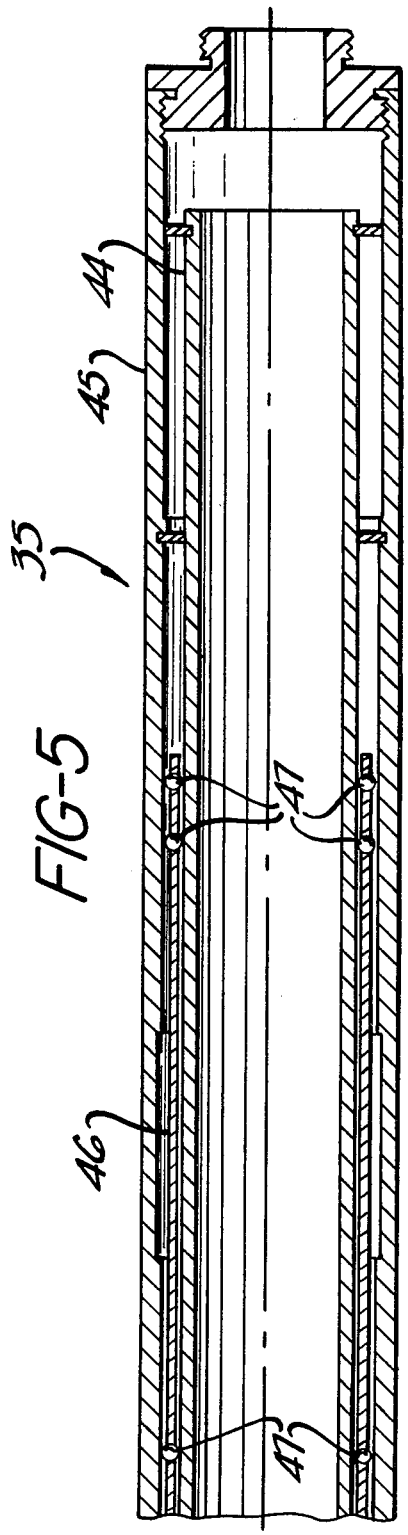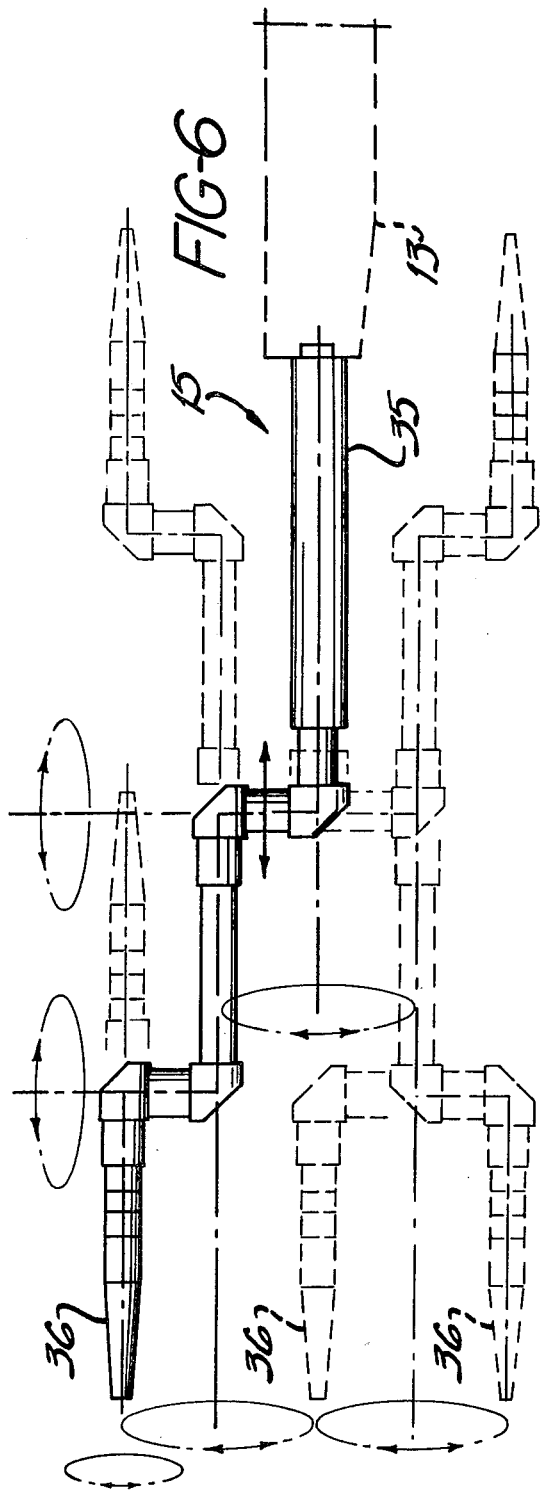

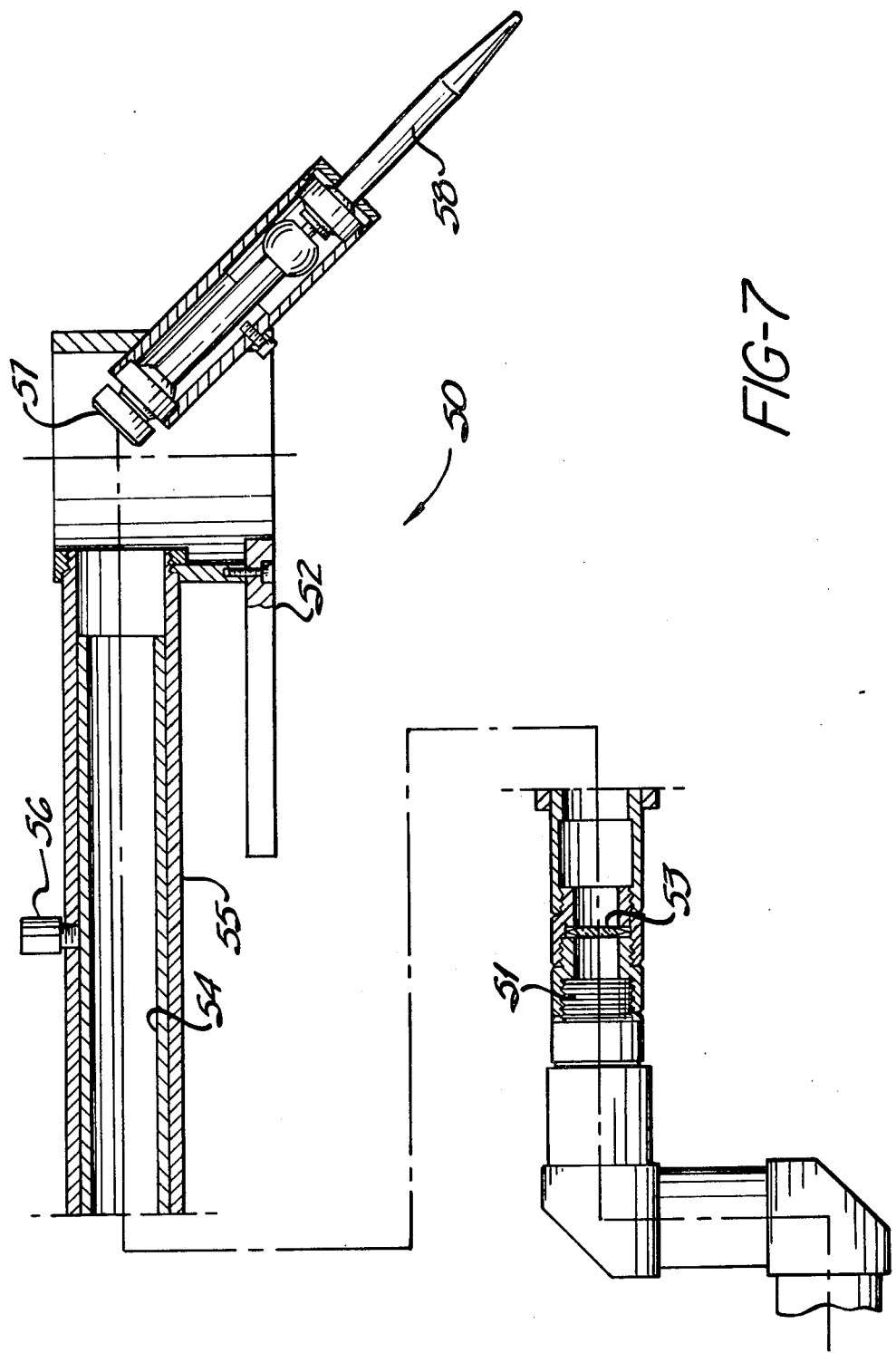

MICROSURGICAL LASER DEVICE

TECHNICAL FIELD

The present invention relates to an apparatus for delivering laser energy to tissues for the purpose of medical intervention in a number of clinical applications.

BACKGROUND ART

The use of focused optical radiation to treat certain problems of the eye began in the early 1950s. The advent of the laser in 1960 made it possible to consider laser optical sources instead of incoherent sources. Lasers offered the advantages of much higher power, narrow wavelength band, smaller focused spot sizes, and better absorption in the target tissues.

Although ophthalmology was the first discipline to use optical radiation to treat disorders, the availability of laser radiation of higher power made it possible to extend the application of lasers to many other medical specialties.

Among the many lasers that have been developed, the carbon dioxide laser, with an emission wavelength of 10.6 microns, offers very useful medical applications because it is absorbed to a very great extent by almost all tissues of the body. Thus, by focusing this laser on tissue, it is possible to photocoagulate, to cut, or to vaporize almost any tissue in the body. Accordingly, the carbon dioxide laser has found application in a number of disciplines such as otolaryngology, neurosurgery, gynecology, and in general surgery, where the laser is used to make incisions with minimum damage to surrounding tissues, to coagulate small arteries and veins, thereby minimizing blood loss, and to vaporize various tumors and abnormal tissues.

A number of instruments have been proposed and a few have been developed for use in a number of applications. These devices typically comprise a laser and an articulated arm with a series of mirrors to direct the beam to the target area. The systems that have been proposed or developed have a number of disadvantages that make their clinical application difficult. Some systems are awkward to use clinically because the laser is directly attached to an operating microscope. In others, the articulated arm contains a large number of mirrors (up to eight mirrors) and has long arms so that the systems require constant attention, extreme care, and repeated realignment in the clinical setting.

SUMMARY OF THE INVENTION

The present invention is directed to overcoming the disadvantages set forth above.

Accordingly, the present invention is designed to be a practical clinical device that is easy to use and requires no adjustments. As compared to previous devices, the subject articulated laser guide arm is shorter and lighter, has fewer mirrors, and requires no adjustment, and indeed, has no adjustments. This articulated arm may be used with a handpiece or it may be attached to an operating microscope via a microscope adaptor.

In a preferred embodiment of the invention, the laser is mounted on a horizontal laser head that contains a carbon dioxide laser, a helium-neon laser for aiming purposes, and a power monitor. This head is supported by a moveable and adjustable support arm that is also articulated and which is suspended from a vertical post. This allows the laser head to be extended and positioned into the proximity of the surgical area by means that does not need to be of optical precision. This permits the use of a shorter and more reliable articulated laser guide arm that nevertheless permits easy manipulation of the laser beam by the operating physician.

The articulated laser guide arm uses only four mirrors, and there are no other mirrors required for the carbon dioxide laser in the system. The articulated laser guide arm also comprises a precision linear bearing in order to provide additional freedom in manipulation of the beam by the physician.

The vertical post is supported by a base cabinet that contains the power supplies and also provides the physician with storage space. The surgical laser that is used in the system is sealed, r-f excited, and air-cooled. This makes the present invention much simpler than other systems that require water cooling and water pumps, a vacuum pump and gas tanks. In addition, unlike other systems where the laser is operating continuously while the system is on, in this system the laser is off until a foot-switch is depressed and only then is the laser turned on for a preset duration or as long as the foot-switch is depressed.

The apparatus employs a moveable control console that is separate from the base cabinet. This contains the controls for the laser power, time of exposure, and on-off switches, and allows for the convenient adjustment of the system characteristics by an operator.

BRIEF DESCRIPTION OF THE DRAWINGS

FIG. 2 is a diagrammatic view of the articulated laser guide arm.

FIG. 3 is an enlarged cross-sectional view of the FIG. 3 bracketed portion indicated on FIG. 2.

FIG. 4 is an enlarged cross-sectional view of the FIG. 4 bracketed portion indicated on FIG. 2.

FIG. 5 is an enlarged cross-sectional view of the FIG. 5 bracketed portion indicated in FIG. 2.

FIG. 6 is an elevational view of the articulated laser guide arm in several of its possible orientations demonstrating several degrees of freedom.

FIG. 7 is a detailed elevational view partly in cross-section of the microscope adapter according to the present invention.

DESCRIPTION OF THE PREFERRED EMBODIMENT

Figure 1:
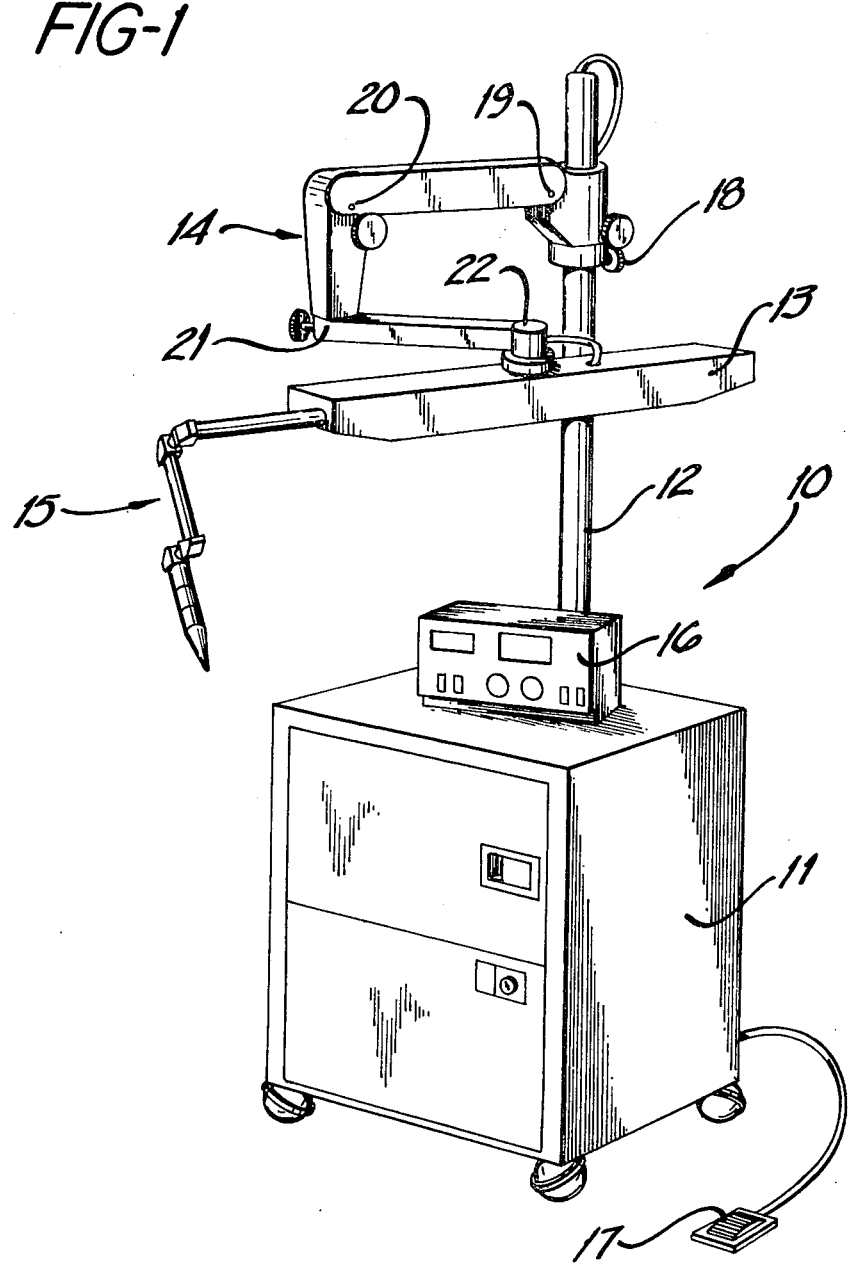
FIG. 1 is an overall perspective view of an illustrative mircosurgical laser system according to the invention including a cabinet, a control console, a laser head, a support arm, and an articulated laser guide arm.

FIG. 1 shows an overall schematic view of the present invention, the microsurgical laser system 10. The laser system comprises a base cabinet 11 that contains power supplies and associated electronics. Supported by the base is a vertical post 12 that supports a laser head 13 by the use of a counterbalanced articulated support arm 14. The laser head 13 contains in its housing a carbon dioxide laser used for treatment, such as a Laakmann Electro-Optics Inc. RF $CO_2$ Waveguide Laser, and a helium-neon laser used for aiming purposes since the beam of the carbon dioxide laser is invisible to the eye. The beams of the two lasers are combined by a method well known to those familiar with the art and are directed into an articulated laser guide arm 15. The laser system is controlled by the use of a control console 16 that has provisions for switching the carbon dioxide and helium-neon lasers on or off, for adjusting the power level of the carbon dioxide laser, and for setting the length of time the carbon dioxide laser will be delivered when a foot-switch 17 is activated by an operating physician.

With further reference to FIG. 1, the support arm 14 is rotatable about post 12 and can be raised or lowered on the post and locked at a desired height by lock knob 18. Alternatively, the post may be made vertically telescopic to vary the height of the support arm 14. The laser head 13 may be raised or lowered easily by the motion of the counterbalanced arm 14 about elbow joints 19 and 20. The laser head 13 is extendable and rotatable in any direction by rotation of the arm 14 about parallel but spaced apart vertical axes defined by joints 21 and 22. Thus, the laser head can be positioned in the desired area in the proper horizontal orientation for the medical procedure. This mobility of the laser head allows for the use of a short and dependable articulated arm 15 for the delivery of the laser beams.

The operation of the microsurgical laser system is as follows.

The position of the laser head 13 is adjusted as outlined above so that the desired extension of the system is obtained. The desired lasers are switched on by the controls on the control console 16, the power is adjusted to the desired level and the time of exposure is set to a predetermined value or is set on continuous. For all settings, the foot-switch 17 is the control for initiating as well as, in the case of continuous settings, for terminating the exposure. The laser beam is brought to the target by the physician using the articulated arm 15 which may be attached either for a handpiece delivery or for delivery through a microscope adaptor as will be described below.

The articulated laser guide arm 15 that is used in the system is shown schematically in FIG. 2. The articulated arm 15 includes a series of four beam redirecting means such as mirrors 31, 32, 33, and 34 each of which is placed in a housing that contains precision bearings. A detail of these housings is shown in FIGS. 3 and 4 which illustrate the precision with which the articulated arm is designed and constructed. For example, the first mirror 31 is located precisely at the correct location on the surface 40 precision defined by machined shoulder 140. Mirror 31 is urged into position abutting against shoulder 140 and locked into place by the use of a threaded annular retaining member 41 and resilient means such as O-ring 42. This arrangement obviates the need for adjustment and alignment of the arm upon assembly or in its operation in the clinical setting. The laser beam always travels along the axis of each section of the articulating arm 15 and eliminates one of the most recurring problems of other laser systems, i.e., the misalignment of the articulated arm. Each housing contains two precision bearings 43.

Referring again to FIG. 2, in order to provide the degrees of freedom necessary for the articulated arm, as shown schematically in FIG. 6, a precision linear bearing 35 is included in the arm. This linear bearing section is shown in greater detail in FIG. 5. Referring now to FIG. 5, it is seen that the linear bearing 35 consists principally of two accurately honed cylindrical sections or tubes, an inner piece 44 and an outer piece 45. The inner tube 44 is threaded at one end and screws into the first mirror housing containing mirror 31 and the outer tube is threaded at one end and screws into the laser head 13. There is a thin cylinder 46 between these two tubes that contains holes for ball bearings such as 47 that allow for the rotation and the linear motion.

Because of the precision with which the articulated arm 15 is machined and assembled, using operations well known to those familiar with the art, the articulated arm needs no alignment. This arm is a very reliable method of delivering the laser beams to the target. The arm can be shorter than in other systems, as discussed previously, because the laser head 13 to which it is attached can be positioned in the vicinity of the target.

The system is designed to have a minimum number of mirrors and the only requirement for alignment is to direct the laser beams into the articulated arm. This is accomplished by the use of conventional adjustments of the laser mounts in the laser head.

As discussed previously, the laser system of the present invention makes use of an articulated arm to deliver the laser beams to the target. As shown in FIG. 3, the end of the articulated arm may be fitted with a handpiece 36. By placing a focusing lens 37 downstream of the last mirror 34, the physician can then manipulate the handpiece and direct the focused beam of the carbon dioxide laser at the targets of interest using the helium-neon laser beam for aiming. It is to be noted that by placing a lens 37 of short focal length a very small spot size can be obtained at the focal plane and with the laser operating in the $TEM_{00}$ mode as is well known to those familiar with the art.

In the present invention it is possible to obtain larger spot sizes out of the handpiece by using different lenses. The lens 37 can be removed. Another lens, of longer focal length, can then be inserted in the articulating arm at location 38 for example, as shown in FIG. 4, in order to provide a larger spot size at the output end of the handpiece. This is useful in certain procedures where a larger spot size is more practical such as, for example, in performing a turbinectomy in the nose as has been done by some physicians. If on the other hand a small spot size is required, for the purpose of cutting tissue for example, then the short focal length lens 37 is inserted and the lens at position 38 is removed.

Another important method of applying a carbon dioxide laser is with an operating microscope. For this purpose, a microscope adaptor 50, as shown in FIG. 7, is used. The handpiece is removed from the end of the articulated arm and the articulated arm is attached to the microscope adaptor by use of a threaded endpiece 51. The microscope adaptor 50 is attached to an operating microscope by the use of a standard dovetail connection 52. The adaptor contains a lens 53 that serves to focus the laser beams on a plane that is parfocal with microscope viewing optics. In order to adapt to various microscope objective lenses, the adaptor 50 makes use of a sliding tube 54 that is moved within an outer tube 55 and can be locked at calibrated positions by lockscrew 56. The laser beams reflect from mirror 57 to the target area. This mirror 57 can be accurately manipulated to the various targets by the physician by the manipulation of a joystick 58. The use of the microscope adaptor 50 on an operating microscope allows the use of the present carbon dioxide system in a number of applications in otolaryngology, neurosurgery, and gynecology.

I claim:

1. Apparatus for guiding a laser beam comprising:
   (a) a support arm;
   (b) a laser head connected to said support arm in a manner to permit said laser head to rotate about a first axis and housing therewithin a surgical laser that emits a beam invisible to the human eye and a second laser capable of emitting a laser beam for aiming purposes visible to the human eye, and means for aligning the two laser beams;

(c) an articulated laser guide arm connected to said laser head for receiving said aligned laser beams and guiding said laser beams from said laser head to a desired target site, said articulated arm including:

(i) a series of beam redirecting means for successively redirecting the laser beams so that the beams are reflected 90 degrees at each redirecting means along a plane perpendicular to the prior direction of the beams; and (ii) a plurality of housings, each associated with one redirecting means for supporting said redirecting means, each housing including a precision shoulder member and means for retaining said redirecting means against one of said shoulder members in such manner that no directional adjustment is required of any of said redirecting means to maintain alignment of said laser beams while said laser guide arm is articulated.

2. The apparatus according to claim 1 further comprising vertical support means on which said support arm is rotatably mounted at a selectable vertical position and wherein said support arm is hinged to provide elevational adjustment positioning of said laser head while maintaining said laser head generally horizontally level without altering the vertical mounting position of said support arm on said vertical support means.

3. The apparatus according to claim 2 wherein said vertical support means is telescopic to permit elevational adjustment of said support arm without altering the vertical position at which said support arm is mounted on said support means.

4. The apparatus according to claim 1 which includes no more than four beam redirecting means.

5. The apparatus according to claim 1 wherein each of said means for retaining each of said redirecting means includes an annular retaining member threadably engaged in said articulated laser guide arm at a 45 degree angle relative to the path of the laser beams that are redirected by the redirecting means of its associated housing.

6. The apparatus according to claim 1 further comprising a console physically separated from said laser head but in data communicating relation with both of the lasers in said laser head for controlling their operation.

7. Apparatus for guiding a laser beam comprising:

(a) a counterbalanced hinged support arm;

(b) an elongated laser head rotatably connected to said counterbalanced support arm in a manner to permit said laser head to rotate about a first axis, and to be elevated or lowered by said support arm as required, said laser head housing an rf excited $CO_2$ waveguide laser for emitting an infrared laser beam and a helium neon laser for emitting a laser beam visible to the unaided human eye to permit directing said infrared laser beam, alignment means to align the two laser beams;

(c) an articulated laser guide arm threadably connected at one end thereof to said laser head for guiding the aligned laser beams from said laser head to a desired target site, said articulated laser guide arm including a telescopic section adjacent said laser head;

(d) a series of four mirrors for successively redirecting the aligned laser beams so that the beams are reflected 90° at each mirror along a plane perpendicular to the prior direction of the beams; and (e) precision means for supporting each of said mirrors, each of said means including a precision machined shoulder member and an annular retaining member threadably engaged in said articulated laser guide arm at a 45 degree angle relative to the path of the aligned laser beams redirected by the mirror associated with said precision means for urging said mirror against said shoulder member, such that each mirror is prealigned and requires no adjustment.

* * * * *